United States Patent [19]

Ernst

[11] 4,107,978

[45] Aug. 22, 1978

[54] DUROMETER ACCORDING TO ROCKWELL SYSTEM

[76] Inventor: Alfred Ernst, Casa Carolina, Curio Ticino, Switzerland

[21] Appl. No.: 772,483

[22] Filed: Feb. 28, 1977

[30] Foreign Application Priority Data

Mar. 1, 1976 [CH] Switzerland .................... 2526/76
Mar. 1, 1976 [CH] Switzerland .................... 2527/76

[51] Int. Cl.² ............................................. G01N 3/44
[52] U.S. Cl. .................................................. 73/83
[58] Field of Search ............................. 73/81, 83, 94

[56] References Cited

U.S. PATENT DOCUMENTS

| | | | |
|---|---|---|---|
| 1,661,718 | 3/1928 | Davis | 73/81 |
| 2,804,769 | 9/1957 | Clark | 73/81 |
| 3,182,491 | 5/1965 | Tschirf et al | 73/83 |
| 3,200,640 | 8/1965 | Ernst | 73/81 |
| 3,965,727 | 6/1976 | Argabrite | 73/81 |

*Primary Examiner*—Anthony V. Ciarlante
*Attorney, Agent, or Firm*—Michael J. Striker

[57] ABSTRACT

An apparatus for testing the hardness of a workpiece has a lower structure having a surface defining a reference plane from which can project an axially displaceable penetrator. A preload spring biases the penetrator with a relatively small preload force into a position projecting from the plane. Upper structure adapted to receive an applied load force directed axially toward the lower structure is displaceable through a long axial distance between an upper rest position relatively far from the lower structure and a lower position directly abutting the lower structure. Intermediate structure is axially displaceable between the upper and lower structures toward the upper structure from a lower position resting on an abutment fixed on the upper structure. This intermediate structure is spaced axially a relatively short distance from the penetrator in the lower position of the intermediate structure and upper position of the upper structure so that displacement of the upper structure down from its upper rest position first engages the intermediate structure with the penetrator and thereafter engages the upper structure directly with the lower structure. A load spring between the intermediate structure and the upper structure urges the intermediate structure against the abutment with a predetermined relatively large load or test force. An indicator reads out the extent of projection of the penetrator beyond the plane.

12 Claims, 3 Drawing Figures

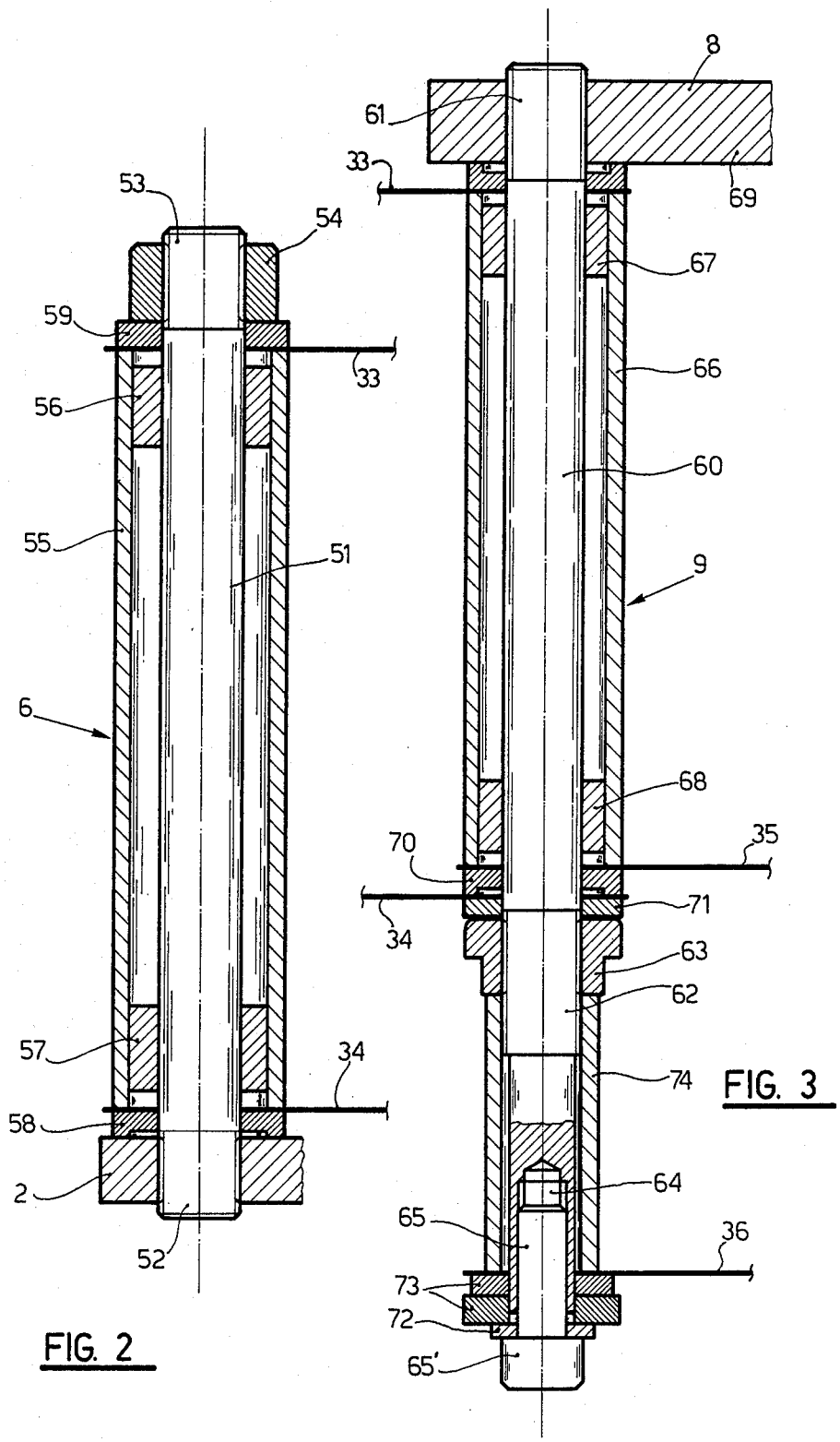

DUROMETER ACCORDING TO ROCKWELL SYSTEM

The present invention relates to a durometer according to Rockwell system.

The object of the invention is to provide an instrument based on Rockwell measurement system, which acts by means of a simple forward and reverse motion and such that, during the measurement, only the reference plane and the penetrator contact the piece to be tested, so that even short surfaces can be checked.

Another object of the invention is to render the measurement load constant while the applied load changes even if said measurement load can be predetermined within a large range of values.

Another object is to have a simple, solid and accurate instrument to be emploied even by applying it on machine tools existing nowadays, for example on the spindle of a drilling machine.

Another object of the invention is to eliminate the clearances and the frictions among the movable members and to produce instruments of reduced sizes, easy production and assembly while assuring a very good accuracy.

Said durometer is characterized by an upper structure, supporting the element receiving the outer applied load and the measurement load spring; by a lower structure provided with the reference plane as well as the penetrator and the members amplifying the relative movement between the penetrator and the reference plane, and further by an intermediate structure interposed between the measurement load spring and the penetrator. Under the application of the outer applied load, the upper structure can move relative to the lower one of a predetermined extent comprised between the resting position and a stop abutment, so that the measurement load spring is subject to a constant deformation to transmit to the penetrator the constant measurement load due only to its deformation, while the exceeding portion of the outer applied load is discharged on the reference plane.

In a preferred and characteristic embodiment of the invention the members provided with a relative displacement are connected together by means of resilient strips rigidly secured thereto, and guided by said strips so that they can displace only parallely to the axis of the penetrator.

A not limitative example of embodiment of the invention is shown in the accompanying drawings, wherein:

FIGS. 2 and 3 show, in section, two different columns to which resilient strips are secured.

Figure 1:
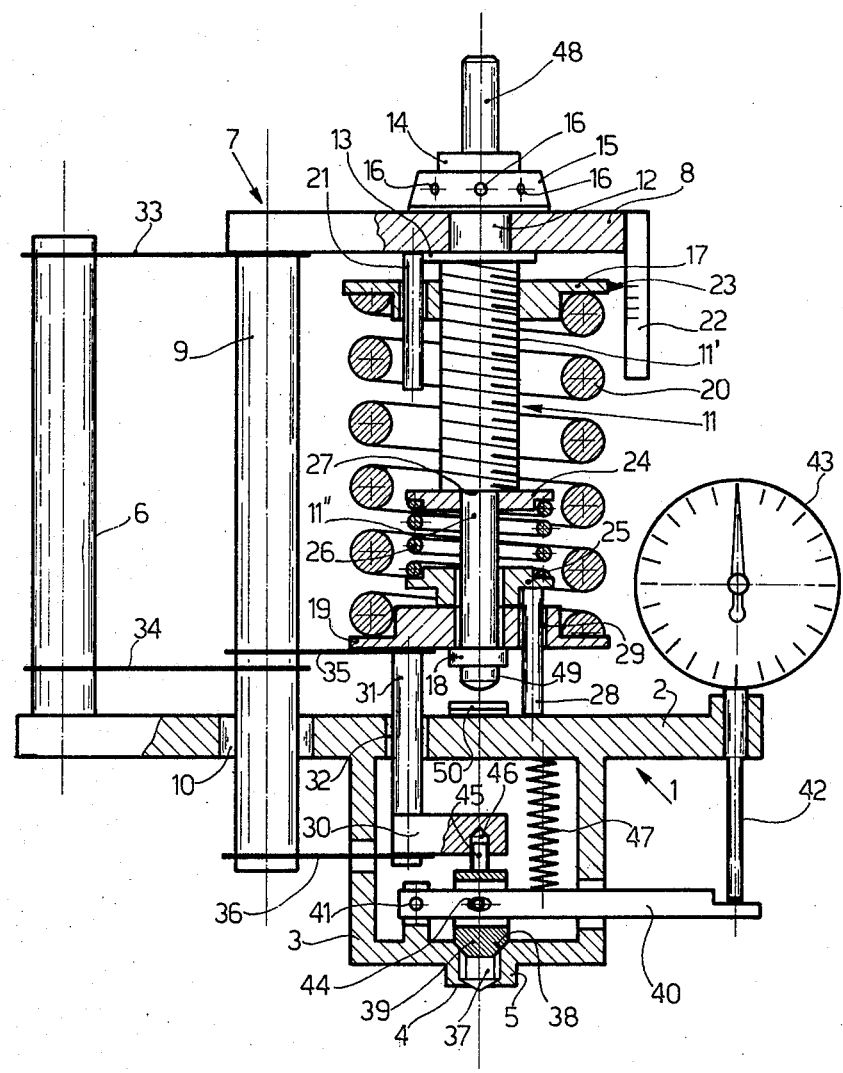
FIG. 1 is a diagrammatical view of the instrument partially in section.

With reference to FIG. 1, the instrument of the invention is composed by a rigid lower structure or resting structure 1, comprising an horizontal stout plate 2, which is integral part of a lower support 3 ending downwards with the reference plane 4 constituted by the edge of a bush 5, in which the penetrator is coaxially housed and can axially slide during the successive steps of the measurement.

An upwardly directed vertical column 6 is rigidly connected to the plate 2.

An upper structure 7 of the instrument is composed by a plate 8 parallel to the plate 2 and a vertical column 9 downwardly directed and parallel to the column 6 is rigidly connected thereto. The column 9 extends below the plate 2, through a loose hole 10 provided on the latter.

The plate 8 supports the rod 11 serving for the transmission of the outer applied load, said rod being fixed at said plate by means of a neck 12 placed inside a coaxial hole, provided on the plate 8, and prevented from the axial displacement relative to the plate 8 by a lower shoulder 13 and by an upper nut 14 with interposition of a ring nut 15 provided with radial holes 16 spaced along its circumference.

The rod 11 is rotatable around its own axis and its rotation can be obtained acting on the ring nut 15, rotating the same by means of pin members inserted into the holes 16.

The portion of the rod 11 extending below the shoulder 13 presents a threaded portion 11' on which a shoulder flange 17 is screwed, while the terminal portion 11" has a smooth surface and ends with an annular abutment 18 serving to support a counter-flange 19. Between the flange 17 and the counter-flange 19 it is shouldered a spring 20 serving to provide the constant measurement load, in the manner hereinbelow explained.

The flange 17 is prevented from rotating by a vertical pin 21 depending from the plate 8 so that rotating in either direction the rod 11, acting on the ring nut 15, said flange 17 can screw in either direction relative to the same rod 11 and then pre-loading the spring 20 at apredetermined value. This value can be controlled by a graduated scale shown by the vertical strips 22 and along which an index 23 supported by the flange 17 slides.

Around the cylindrical portion 11" of the rod 11, two small spaced flanges 24 and 25 are provided, between which a coil spring 26 acts so that the flange 25 in resting position of the instrument abuts against the flange 19, while the flange 24 is thrusted against the shoulder 27 constituted by the step formed by the diameter difference between the portions 11' and 11" of the rod 11.

The flange 24 is assembled in a free condition on the portion 11".

The flange 25 is rigidly connected to the plate 2 by means of one or more vertical pins 28.

A third rigid structure, intermediate between the structures 1 and 7, is constituted by the same flange 19, by a thrusting member 30 placed under the plate 2 and by a vertical column 31, rigidly connecting the flange 19 and the thrusting member 30 and passing the plate 2 through a loose hole 32.

The column 31 is parallel to the columns 6 and 9.

The columns 6 and 9 are connected therebetween by two elastic strips 33 and 34, preferably of steel material, whose ends are tightened without any clearance at the same columns. This connection allows a mutual support between the structures 1 and 7, as well as a relative displacement without any clearance between said structures, said displacement can be considered axial in the direction of the same columns and the rod 11, owing to its limited value in the operation of the instrument.

Similarly the intermediate structure, and particularly the column 31, is connected to the column 9 by a respective pair of parallel elastic strips 35 and 36, so that the intermediate structure is connected to the structure 7 and is subject to little axial displacements with respect to the latter, without any clearance.

The pairs of strips 33 and 34, on the one hand and 35 and 36 on the other hand constitute the same number of parallelograms with the columns by them connected, so that the bending of the strips secures the axiality of the relative displacement between the columns. The formed parallelograms are preferably rectangular, so that the relative displacements of the columns can be considered straight-line with a good approximation.

Axially to the rod 11, it is provided the penetrator 37 which is housed in the bush 5, supporting the reference plane 4, and whose point of diamond or other hard material, is apt to come out besides said reference plane of a portion determined by a conical abutment 38. The penetrator 37 is supported by a penetrator holder 39 which, in its intermediate portion, is hollow to be passed through by a lever 40 which, from one end, has its fulcrum in 41 and, to the other end, comes out from the support 3 to support the rod 42 operating the comparator 43, the latter being a reading instrument already known, of the type with manual or automatic zeroing.

Said comparator 43 is not further described because it is certainly known from the skilled in the art.

The lever 40 is connected to the penetrator holder 39 by means of a pin 44, passing in an elongated hole of the same lever.

Upwardly the penetrator holder is prolonged with a stem 45 entering inside a hole 46 praticated on the thrusting member 30, the hole always in axis with the rod 11.

Between the lever 40 and the plate 2 it is disposed a spring 47 designed to provide the preload during the measurement, in the manner hereinbelow explained, said spring providing a thrust considerably inferior than the thrust provided by the spring 26 already discussed.

The rod 11 shows upwardly a stem 48 so sized and projecting that can be tightened by the toolholder head of a spindle having an axial movement and operated only with this movement, that is without any rotation. Besides the stem 48 can be provided for the assembly of the instrument on an adequate equipment, able to exert an axial thrust on the rod 11.

At the bottom, the rod 11 presents a rounded end 49 which, at rest, is placed at a predetermined distance relative to an abutment 50 preferably of yelding damping material or resting in any case on the plate 2 with the interposition of a damping shim, such an abutment defining the operating stroke of the rod 11 and therefore the deformation value of the spring 20 for the transmission of the constant measurement load to the penetrator. The damping nature of the abutment 50 is provided only to eliminate vibrations when contacted the end 49. Said abutment 50, however, constitutes a fixed stop point between the upper structure 7 and the lower structure 1, said point being disposed on the penetrator axis.

FIG. 2 shows, in section, the structure of the column 6 and the stiff tightening manner thereon of the strips 33 and 34. The column 6 is composed by a central rod 51, whose lower end 52 is threaded and screwed in a hole provided in the plate 2, while its upper end 53 is threaded too for the engagement of a nut 54.

The rod 51 is surrounded by a cylindrical sleeve 55, in register with the rod 51 by spaced cylindrical shims 56 and 57. Said sleeve 55 presses with its lower edge against the strip 34 supported by an annular washer 58, the latter in turn abutting against the plate 2. The upper end of the sleeve 55 presses against the strip 33 upwardly shouldered by a ring 59. On said ring 59 acts the nut 54. It is evident that a strong tightening of all the members comprised between said nut and the plate 2 will take place on screwing the nut 54 on the threaded end 53, so that the strips 33 and 34 will result rigidly locked, without any possibility of clearance.

FIG. 3 is an axial section of the column 9 illustrating the structure of this column and the tightening thereon of the strips 33, 34, 35 and 36.

The column 9 is composed by a long rod 60 having its upper end 61 threaded so that it is screwed on the plate 8 of the member 7.

The rod 60 presents, further, an intermediate threaded portion 62, around which a nut 63 is screwed, and a lower end provided with an axial dead hole 64 into which a bolt 65 is screwed.

Around the rod 60 it is disposed a first sleeve 66, similar to the sleeve 55 of FIG. 2, which is kept in register with respect to the rod 60 for interposition of cylindrical shims 67 and 68 respectively. On the top the sleeve 66 presses on the resilient strip 33 passed by the same rod 60 and resting on a ring 69 which abuts against the lower face of the plate 8. At the bottom the sleeve 66 presses on the resilient strip 35 and, with the interposition of an annular washer 70, presses also on the strip 34 shouldered by the nut 63 with the interposition of a washer 71.

It is evident that, on screwing the nut 63, all the members comprised between the same nut and the plate 8 are locked together and therefore the strips 33, 34 and 35 remain tightened, without any possibility of clearance.

The head 65' of the bolt 65, by means of a washer 72 and one or more annular shims 73, presses axially against a second sleeve 74, surrounding the lower portion of the rod 60 and abutting against the lower edge of the nut 63. Between the shims 73 and the edge of the sleeve 74 is interposed the resilient strip 36 passed by the same rod 60. In this manner by tightly screwing the bolt 65, the locking of all the members comprised between the head 65' and the nut 63 is caused, locking the strip 36 without any possibility of clearance.

The strips 35 and 36 are locked on the column 31, in a manner similar to FIG. 2, concerning the column 6, even if with members proportioned in size with respect to the sizes of the column 31.

The operation of the instrument so described is explained hereinbelow.

Acting on the ring nut 16, the rod 11 is rotated in either direction, therefore the flange 17 raises or lowers so to supply the spring 20 with a precompression, to which will correspond, owing to the constant deformation, a predetermined measurement load, legible on the scale of the strip 22.

The instrument is then applied on the tool or the machine-tool, for example a drilling-machine, by means of which the same instrument can be operated and approached to the piece to be measured.

At the end of the approachment, the penetrator tip 37 will touch the piece and will be then pushed backwardly in the bush 5, up to the reference plane 4 touches the piece. The displacement of the penetrator relative to the reference plane causes at the same time the deformation of the spring 47, which supplies the preload to the penetrator, and the displacement of the rod 42 acting on the comparator 43. At this moment, the comparator 43 is zeroed, manually or automatically, according to the kind of comparator emploied and the applied outer load is prosecuted. Going on with the thrust, the column 28 prevents the flange 25 from displacing downwardly, therefore the counter-flange 19 is detached therefrom so that it is not influenced by the spring 26, but it is only subject to the thrust of the spring 20. Going on with the displacement of the rod 11, the bottom of the hole 46 will engage the head of the stem 45, beginning to press the tip of the penetrator 37 against the piece. In this moment, the flange 19 will be stopped by the column 31 detaching from the shoulder 18, as the rod continues freely its travel together with the structure 7, whose column 9 can move relative to the columns 6 and 31 thanks to the resiliency of the strips 33 and 34, on the one hand, and 35 and 36 to the other hand.

The displacement of the rod 11 will continue up to the end 49 arrives to touch against the abutment 50.

In this moment on the thrusting member 30 will act the whole load of the spring 20, while on the structure 1 and therefore on the reference plane 4, the exceeding of the outer applied load will discharge. Therefore, at this point, on the penetrator will act the preload and the load of the spring 20, whose total amount is the measurement load.

In these conditions the diamond point of the penetrator 37 will cause the measurement impression.

At this moment the return stroke of the rod 11 can be started.

During the return stroke, firstly the detachment of the end 49 of the rod from the abutment 50 will take place until the shoulder 18 rests again on the counterflange 19 raising the latter, so that the bottom of the hole 46 of the thrusting member 30 detaches from the penetrator, on which only the preload spring 47 will act again. At this point the measurement of the hardness on the comparator is effected according to Rockwell process.

Continuing the raising of the rod 11, the contact between the flange 19 and the small flange 25 will take place again, ending the raising of the rod 11 and coming back the whole to the resting position. The cancellation of the thrust causes the whole to lose the contact with the piece to be tested.

It can be noted in FIGS. 1, 2 and 3 that the pairs of columns 6 and 9 and the corresponding resilient strips 33 and 34, on the one hand, and the pairs of columns 9 and 31 with the corresponding resilient strips 35, 36 to the other hand, constitute two different parallelogram resilient suspensions, whose strips form arms with equal length and of equal resilient deformation, to secure displacements which, owing to the limited amplitudes of the moving parts, are to be considered axial.

It can be also noted that the different moving parts do not present guiding fits in the axial displacement, and this makes easier the instrument both for the reduction of the component pieces, for the elimination of the delicate machinings necessary, for the simplification of the assembly operations and for the elimination of frictions.

Notwithstanding that in the figures the strips are directed perpendicularly to the column axes, it is preferable that on rest, they are inclined relative to the perpendicular to said axes of about half of the foreseen displacement, to the end to render practically unappreciable the transversal displacements, relative to the axial work displacements.

It is obvious that the practical embodiment of the instrument of the present invention can be varied both in the disposal and in the shape of the various members in order to respond to the common requirements of the instruments of this kind, above all as far as it concerns the axiality of the movements and the thrust truing. For example the columns 6 and 9 both indicated in the figures on the same side of the instrument, in practice they will be disposed symmetrically relative to the rod 11.

Further the column 31 can be double to prevent yeldings during the transmission of the load, as well as the bush 5 and the penetrator will be detachable to allow the replacement.

What I claim is:

1. An apparatus for testing the hardness of a workpiece, said apparatus comprising:
    lower structure having a substantially planar surface defining a reference plane;
    a penetrator displaceable along a penetrator axis relative to said lower structure between an outer position projecting relatively far from said plane and an inner position generally flush with said plane;
    a preload spring between said penetrator and said lower structure urging said penetrator into said outer position with a relatively small preload force;
    upper structure adapted to receive an applied load force directed axially toward said lower structure;
    means between said upper and lower structures for axial displacement of said upper structure relative to said lower structure through a relatively long axial distance between an upper rest position relatively far from said lower structure and a lower position abutting said lower structure;
    an abutment carried on and axially displaceable with said upper structure;
    intermediate structure axially displaceable toward said upper structure from a lower position resting on said abutment, said intermediate structure being spaced axially a relatively short distance from said penetrator in said lower position of said intermediate structure and said upper position of said upper structure, whereby displacement of said upper structure from said upper position engages said intermediate structure with said penetrator and thereafter engages said upper structure directly with said lower structure; and
    a load spring between said intermediate structure and said upper structure urging said intermediate structure against said abutment with a predetermined relatively large load force.

2. The apparatus defined in claim 1, further comprising a plurality of resilient strips each having one end connected to one of said structures and another end connected to another of said structures.

3. The apparatus defined in claim 1 wherein said upper structure includes:
    a support plate;
    a spindle rotatable about said axis, extending therealong, and axially fixed in said support plate;
    a flange threaded on said spindle and engaging an end of said load spring; and
    means for inhibiting rotation of said flange relative to said support plate, whereby rotation of said spindle screws said flange along said spindle and changes the compression of said load spring.

4. The apparatus defined in claim 3 wherein said abutment is formed on said spindle, said intermediate structure including a counterflange engaging the other end of said load spring and lying on its said lower position on said abutment.

5. The apparatus defined in claim 1, further comprising means including an indicator for indicating the position of said penetrator relative to said plane.

6. The apparatus defined in claim 1, further comprising a thrust spring braced directly between said lower structure and said upper structure and urging said upper structure into said upper rest position with a force greater than said preload force.

7. The apparatus defined in claim 1 wherein at least one of said structures is provided with a column extending axially and an other of said structures is formed with a throughgoing guide hole spacedly receiving said column.

8. An apparatus for testing the hardness of a workpiece, said apparatus comprising:
lower structure having a substantially planar surface defining a reference plane;
a penetrator displaceable along a penetrator axis relative to said lower structure between an outer position projecting relatively far from said plane and an inner position generally flush with said plane;
a preload spring between said penetrator and said lower structure urging said penetrator into said outer position with a relatively small preload force;
upper structure adapted to receive an applied load force directed axially toward said lower structure;
means between said upper and lower structures for axial displacement of said upper structure relative to said lower structure through a relatively long axial distance between an upper rest position relatively far from said lower structure and a lower position abutting said lower structure;
an abutment carried on and axially displaceable with said upper structure;
intermediate structure axially displaceable toward said upper structure from a lower position resting on said abutment, said intermediate structure being spaced axially a relatively short distance from said penetrator in said lower position of said intermediate structure and said upper position of said upper structure, whereby displacement of said upper structure from said upper position engages said intermediate structure with said penetrator and thereafter engages said upper structure directly with said lower structure;
a load spring between said intermediate structure and said upper structure urging said intermediate structure against said abutment with a predetermined relatively large load force; and
a plurality of generally parallel resilient strips each having one end secured to one of said structures and another end secured to another of said structures.

9. The apparatus defined in claim 8 wherein said one of said structures is provided with a column extending parallel to said axis and secured to said one ends, said other structure being formed with a throughgoing hole spacedly receiving said column.

10. The apparatus defined in claim 9 wherein said other member is provided with a second column secured to said other ends and parallel to the first mentioned column.

11. The apparatus defined in claim 8 wherein said strips extend generally perpendicular to said axis.

12. The apparatus defined in claim 8 wherein said strips are elastically deformable.

* * * * *